United States Patent [19]
Aguilar et al.

[11] Patent Number: 5,578,017
[45] Date of Patent: Nov. 26, 1996

[54] ENEMA NOZZLE WITH SELF-ADHESIVE SECURING MEANS

[76] Inventors: John M. Aguilar, Rte. 1, Box 161, Sweeny, Tex. 77480; Daniel S. Goodin, 431 Lamar, #56, West Columbia, Tex. 77486

[21] Appl. No.: 432,567

[22] Filed: May 1, 1995

[51] Int. Cl.$^6$ .................................................. A61B 5/00
[52] U.S. Cl. ........................................ 604/275; 604/278
[58] Field of Search .................................. 604/275, 278, 604/264, 272

[56] References Cited

U.S. PATENT DOCUMENTS

| | | | |
|---|---|---|---|
| 3,765,413 | 10/1973 | Lepar | 604/278 |
| 3,893,446 | 7/1975 | Miller | 604/278 |
| 3,927,672 | 12/1975 | Garcia | 604/278 |
| 4,096,853 | 6/1978 | Weigand | 604/278 |

*Primary Examiner*—John D. Yasko
*Attorney, Agent, or Firm*—C. Steven McDaniel; Carol G. Mintz; Conley, Rose & Tayon, P.C.

[57] ABSTRACT

A disposable flexible plastic enema nozzle with self-adhesive securing means for convenient attachment to the patient's buttocks is disclosed. The securing means comprises an annular positioning collar disposed about the enema tip or tube. The positioning collar has an elongated self-adhesive plastic sheet with easily removable protective tabs covering the adhesive. In one embodiment of the invention the positioning collar is fixed near the distal end of the tube, while in another embodiment the positioning collar is slidable along the tube for adjusting the insertion length of the tube. The invention is particularly applicable to diagnostic enema procedures, such as barium enema for radiological examination, performed on infants, small children, the infirm and the elderly.

17 Claims, 3 Drawing Sheets

ENEMA NOZZLE WITH SELF-ADHESIVE SECURING MEANS

BACKGROUND OF THE INVENTION

1. Field of the Invention

This invention relates to disposable enema nozzles and more particularly to nozzles with adhesive means for securing the conduit to the body during the enema procedure. Still more particularly, the invention relates to an enema nozzle having an attached external positioning means that permits the technologist to adjust the insertion length of an enema tube.

2. Description of the Related Art

Enema tubes that are conventionally used in medical procedures such as administration of a barium enema for radiological examination, intrarectal administration of medicine, or other procedures where the tube necessarily remains in place for a period of time, typically comprise a smooth rigid or flexible tip or a tip with an inflatable retention cuff. Tips of these types are available, for example, from Lafayette Pharmaceuticals Incorporated, Lafayette, Ind.

Problems are frequently encountered with traditionally used enema tubes particularly when left in place for an extended period of time. Such problems include expulsion of the tip prior to completion of the procedure. Expulsion can occur due to pressure arising from colonic resistance due to distension by the enema fluid or from the opposing natural flow of intestinal contents. Also, some types of enema tubes can be easily dislodged while the technologist is positioning the patient or by the patient's movements during the procedure. This is frequently the case with pediatric patients, particularly infants. Additionally, in some patients, particularly infants and the elderly, the anal sphincter is functionally unable to retain the tip or to close tightly around the tip. As a result, leakage of the enema fluid commonly occurs, often causing insufficient colonic filling. Imperfect procedural results may be obtained as a consequence, or an insufficient dosage of medicine may be received by the patient. Another drawback of known enema nozzles having inadequate securing means is that they can travel too far into the patient's rectum. A particular concern with pediatric patients, who commonly move about during the enema procedure, is avoiding having the tube rupture a fragile rectum wall. Infants expecially have highly variable colonic dimensions which defy uniform treatment methods and materials.

Various prior art devices which employ a contoured region at some point along the tip for engaging the anal sphincter have been developed to deal with the problems of expulsion and fluid leakage around the tip. One such device is described, for example, in U.S. Pat. No. 4,325,370 to Young which discloses a locking groove on the enema tip in combination with a waist band and strap assembly to deter expulsion of the tip and prevent the tip from inappropriate insertion. Such a device is intended to be convenient for a patient to self-adjust, and anticipates that the technologist would then complete the attachment of the enema conduit. While devices such as Young's are an improvement for some patients over an unsecured enema tip, these devices are most appropriate for use with cooperative older children or adult patients. Elderly patients, for example, might find such assemblies uncomfortable or too difficult to adjust. Others, including the very young patient or the infirm, would be unable to use such assemblies. The technologist could be expected to have considerable inconvenience and expenditure of time putting such a device on the patient. Also, various sizes of the waistband/strap device would be needed to accommodate infant through adult-size patients.

Prior art methods simply incorporating an insertable retaining means on the tube, such as by modification of the contour of the tube's insertion end, or by putting an inflatable cuff or balloon on the tube end improves retention in some patients. However, inflation of the balloon in the patient's rectum typically causes discomfort. One such internal retention means is shown, for example, in U.S. Pat. No. 3,990,448 to Mather et al. which discloses a tapered head on the proximal tube end made large enough to deter expulsion and a retaining shoulder on the tube shaft, between which the anal sphincter of an average person is received.

Others have employed anal plugging means attached to the enema tube along with an external securing means to address the leakage, tube shifting and tube dislodging problems. For example, U.S. Pat. No. 3,575,160 to Vass et al. discloses an enlarged tapered head on the end of the inserted tube, a conical stud (located about midway along the tube) which fits within and seals the anal opening, and a plate attached to the stud which engages the bony outlet of the pelvis around the anus and engages the muscular-skin raphe in the cleft space between the buttocks.

While the existing art devices described above address to some degree the leakage and expulsion problems, and some prior devices also comprehend the problem of preventing the tip from being inserted too far into the rectum, they nevertheless have significant drawbacks. For example, most devices are designed to accommodate an average person and do not adequately provide for procedures on infants, very young children, the infirm or many geriatric patients or others without interactive anal muscles. The danger of bowel injury as a result of the enema tube's moving out of position and going too far into the rectum during a procedure is a continuing problem with some devices. There is also the risk with devices employing an inflated cuff of rupturing a fragile rectal wall. Infants, the elderly and others with insufficient rectal wall resiliency are particularly at risk. Use of an inflatable cuff in children under 10 years of age is generally not recommended by those of skill in the art. Even the best commonly used leakage-deterring devices for holding an enema tube in place for the duration of a medical procedure continue to have drawbacks including being uncomfortable or inconvenient for the patient, being excessively time consuming or being cumbersome for the technologist to use. Other devices are uneconomical, and do not adequately provide for wide variance in patient age, physical condition, ability to cooperate and so forth.

In present day practice the methods used by radiology staff typically include using a standard flexible tube, or tip, with a slightly rounded and enlarged head and, prior to insertion of the tip, wrapping one end of each of several strips of surgical tape around the tube at the most suitable position (as estimated by the technologist from age and condition of the patient and the buttocks size). This is followed by inserting the tube and, while the technologist holds the tube in the appropriate position, applying the dangling free ends of the tape strips to the patient's buttocks. One problem frequently encountered includes tangling of the tape strips during placement of the enema tube. Another problem is that once the tube is in place there is no convenient way to readjust placement of the tape wrapped around the tube without removing the tube. Disposable enema nozzles are needed which can be conveniently secured to the patient and which can avoid at least some of the above-described failings of prior art devices.

SUMMARY OF THE INVENTION

The present invention provides an enema nozzle useful, for example, in administering barium enemas for radiological examination, for intrarectally administering medicines, or in other procedures where the enema tube must remain in place in the patient's rectum for an extended period of time. The device of the present invention avoids at least some of the disadvantages of the prior art and is particularly applicable for use in enema procedures for infants and small children, the infirm and geriatric patients.

The nozzle of the present invention provides an easily inserted, standard-type enema tip with a distally attached self-adhesive positioning collar having an elongated adhesive sheet or strip for adhering to the patient's buttocks. For the purposes of this disclosure, "distal" or "distally" are defined as referring to a position that is away from the patient's rectum when the nozzle of the disclosed invention is oriented for its intended use. Likewise, "proximal" or "proximally" refer to a position that is toward the patient's rectum or inward from the rectum when the nozzle of the invention is oriented for its intended use.

Protective tabs cover the adhesive and can conveniently be peeled back and removed to expose all or at least some of the adhesive when the technologist is ready to secure the nozzle. The nozzle is secured by pressing the "sticky" side of the adhesive strip against the patient's buttocks. For the purposes of this disclosure the term "nozzle" refers to the combination of an enema tip, or tube, the external positioning collar, and a conduit connector or adapter.

One embodiment of the invention disclosed herein provides for the positioning collar to be located in a fixed position around the tube at a point distal from the insertion end of the tube. By fixedly positioning the insertion end of the tube at a variety of distances from the collar, a range of sized enema tips may be obtained.

An alternative embodiment of the invention provides for adjustment by the technologist of the positioning collar by sliding it up or down along the shaft of the tube. In the latter embodiment, the positioning collar is held in the desired position away from the tube's rectal entry point by a friction-fitting resilient annular nipple. Thus, the effective length of the enema tube that can be inserted can be made either shorter or longer as is necessary for a particular patient. The technologist does not have to have on hand various length enema tips and can avoid the risks of using a too-long tip. The technologist then squeezes the buttocks tightly together and secures the collar's self-adhesive strip to the patient's buttocks, thereby holding the nozzle in place with relative comfort for the patient.

Securing the enema nozzle of the present invention is quicker and less cumbersome than with traditional devices. The nozzle of the present invention, when secured as disclosed herein, allows the technologist to position the patient during the enema procedure without discomfort for the patient and without appreciable risk of having the tube move too far internally or of being expelled. Also, when using the present invention, unanticipated movement by the patient during the procedure, as is particularly experienced with infants and young children, is less likely to interfere with a procedure than with use of prior art devices. In particular, unwieldy dangling tape strips are avoided by use of the adhesive strips of the invention which are applied much like a Band-Aid® strip is applied. Having the buttocks held tightly against the tip assists the patient with holding the enema fluid in and with keeping the tip in place. When the nozzle of the present invention is used, for a barium enema, for example, only a minimal amount of barium may leak out and the tip cannot be pushed out. Leakage of the enema fluid is minimized as well, by maintenance of the correct tube positioning and by substantially immobilizing the entire nozzle provided by the present invention.

Accordingly, specifically disclosed herein is a disposable enema nozzle which includes a flexible plastic tip, or tube through which fluid can flow from a conduit connector, or adapter, which is attached to tubing connected to an enema bag and can flow out from the other end of the tube via at least one outlet and into a patient's rectum. The tube is held in place in the rectum by a flexible positioning collar, attached at an appropriate site along the length of the tube, which adhesively attaches to the patient's buttocks pressing the buttocks firmly against the tube. The positioning collar includes a self-adhesive sheet for securing the positioning collar/nozzle combination to a patient's buttocks during an enema procedure.

One particular feature of the invention is that the positioning collar may be permanently fixed at the flared-out tube end so that the insertable tube length can be maximized. Alternatively, the positioning collar may be located at any desired point along the length of its shaft by having the nipple of the collar encircle the tube is such a way that it can be manually pushed or pulled along the tube while meeting just enough frictional or other resistance to sliding to keep it in the selected position for the duration of the enema procedure. Therefore, the rectally insertable length of the tube can also be varied as necessary for a particular patient.

The positioning collar holds the tube immobile at the preselected position by means of a flexible plastic sheet which is coated on one side with adhesive for sticking to the patient's buttocks. Easily removeable covers or tabs protect the adhesive until the technologist is ready to press it into place against the skin. The nonadhesive side of the plastic sheet is permanently attached to a flattened-out extension portion formed as a unit with, and out of the same material as, the nipple.

Although it has been shown by the inventors that a suitable shape for the nipple of the positioning collar is frustoconical, or like a cone with the pointed end cut off, the nipple can be flat or another shape, so long as it has an outlet for the tube to extend through and provides an adequate annular attachment surface.

Thus, the present invention comprises a combination of features and advantages which enable it to substantially advance the enema nozzle and diagnostic enema procedures art by providing an economical disposable device for effectively and efficiently positioning and maintaining an enema tube in a patient's rectum with relative ease and comfort for the patient. These and various other characteristics and advantages of the present invention will be readily apparent to those skilled in the art upon reading the following detailed description of the preferred embodiments of the invention and by referring to the accompanying drawings.

BRIEF DESCRIPTION OF THE DRAWINGS

For a detailed description of the preferred embodiment of the invention, reference will now be made to the accompanying drawings, wherein.

DETAILED DESCRIPTION OF PREFERRED EMBODIMENTS

Figure 1:
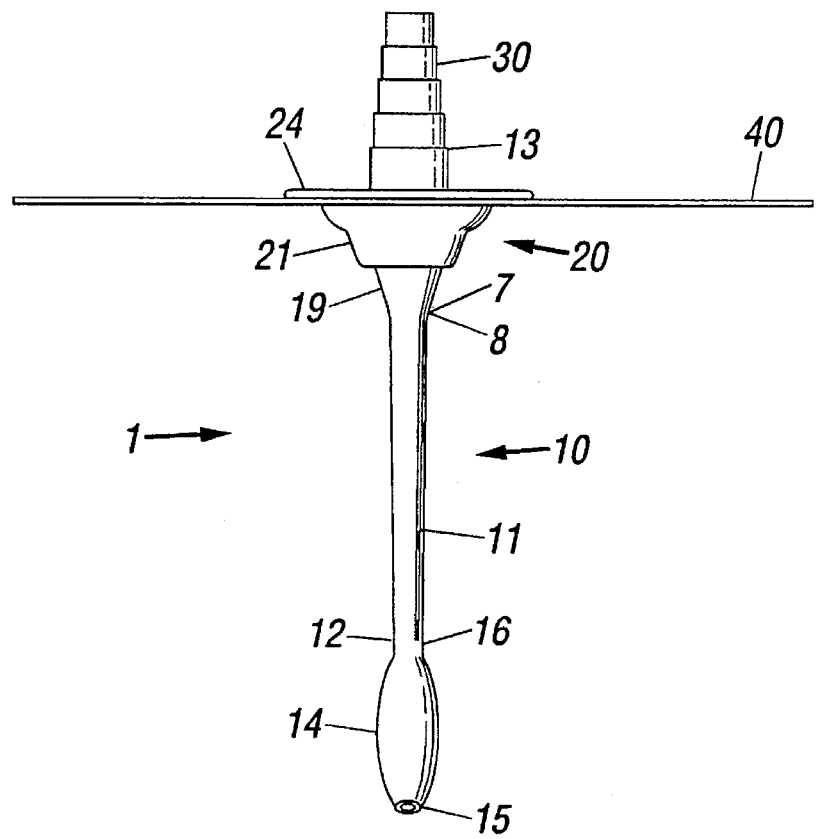
FIG. 1 is a side view of the nozzle of the present invention.

Referring to the attached drawings, and initially to FIG. 1, the disposable enema nozzle of the present invention is shown at 1 and comprises a flexible plastic tip or tube 10, a self-adhesive positioning collar 24 disposed about tube 10, and a rigid plastic conduit connector or adaptor 30 for connecting to a fluid source such as tubing leading from an enema bag. Tube 10 generally comprises a first end 15 (being the initial contact point for placement of the tube 10 into a patient's rectum), a shaft 11 having central longitudinal throughbore 9 (shown in FIG. 6), an expanded or flared portion 19, a second end 13. Tube 10 may be a conventionally known flexible plastic enema tip available from a number of commercial suppliers, for example, such as Lafayette Pharmaceuticals Incorporated, Lafayette, Ind. Tube 10 may be a standard adult size tip having any of a variety of suitable head shapes, it may include an inflatable balloon at the end, or it may be a shorter pediatric size tip. In one embodiment of the present invention the region between shaft first end 12 and first end 15 of tube 10 comprises a bulbous area, terminus 14, in the shape of a truncated ovoid having a central cavity 17 and end 15,16 openings compatible in diameter with that of shaft 11. The first end 15 of terminus 14 is the same as first end 13 of tube 10. The second end 16 of terminus 14 is joined end-to-end with the first end 12 of shaft 11 to provide for continuation of fluid flow from the tube shaft 11 through the terminus 14 and out into the patient's rectum through auxiliary outlets 18 and end 15. The end-to-end junction between end 16 and end 12 is permanently joined. Alternatively, shaft 11 and terminus 14 may be molded as one unit, thereby eliminating the last mentioned joint. Of course, it is possible to fixed by any suitable glue. Tube shaft second end 8 is joined to and integral with an expanded portion 19 of the tube 10, as best shown in FIGS. 5 and 6.

In one embodiment of the invention disclosed herein (shown in FIG. 6) tube 10 is about 7 cm in length; shaft 11 is about 22 mm in length and has a central throughbore 9 that is about 3 mm in diameter; expanded portion 19 is about 2.8 cm in length, and has an increasing external diameter of about 4 to 6 mm from first end 12 to second end 13 of tube 10 and a correspondingly increasing internal bore diameter 6 of about 2 to 5 mm, which larger diameter accommodates first end 31 of adapter 30. In the same embodiment terminus 14 is about 9 mm in length and its diameter varies from about 3 mm at either end 15, 16 to about 4.5 mm at a point about midway along the length of terminus 14. The central cavity 17 of terminus 14 likewise varies in diameter from about 2 to 3.5 mm from either end 15, 16 to about midway on the length of terminus 14. In this embodiment, the auxiliary outlets 18 are pairs of axially opposing openings in terminus 14 that are in communication with the central cavity 17. Each of the auxiliary outlets 18 are about 1 mm in diameter, and one pair of which is positioned at about 1.5 mm from end 15 of tube 10 and the other pair are positioned at about 4 mm from end 15 and are placed at about 180 degrees about the axis of tube 10 relative to the location of the first pair.

Figure 2:
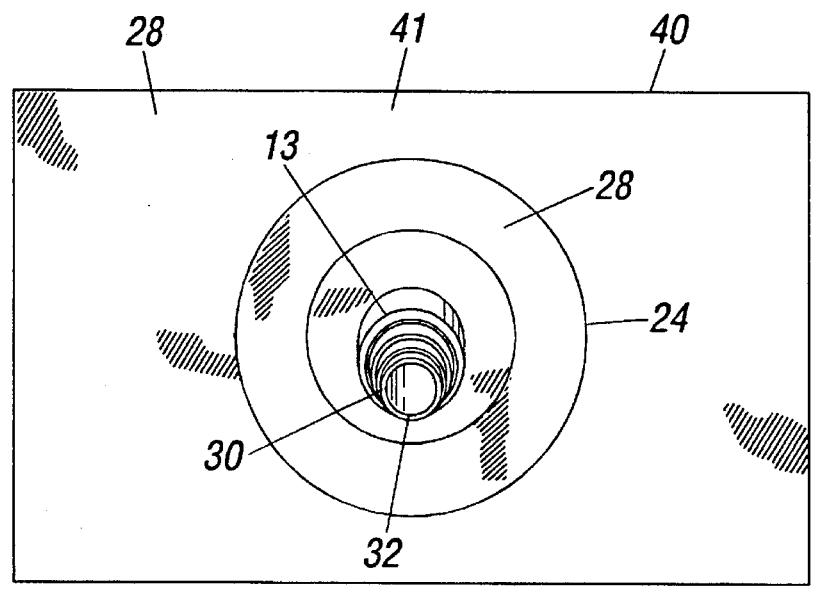
FIG. 2 is a top view of the nozzle showing the tube end, with adaptor attached, extending through the positioning collar, and showing the flat collar extension and the non-adhesive side of the self-adhesive sheet.

The expanded portion 19 of tube 10 may be stretched to accommodate first end 31 of a conduit connector or adapter 30, as depicted in FIG. 2. The dimensions of the expanded portion 19 are not critical so long as the expanded portion can join first end 31 of a suitable adapter 30 and provide a stop for positioning collar 20, as described below. The second end 32 of adapter 30 is shown unattached to a fluid source, which can be conventional flexible tubing leading to an enema bag. The adapter used in this invention can be obtained from any of a number of commercial sources that are well known by those of skill in the art.

Figure 4:
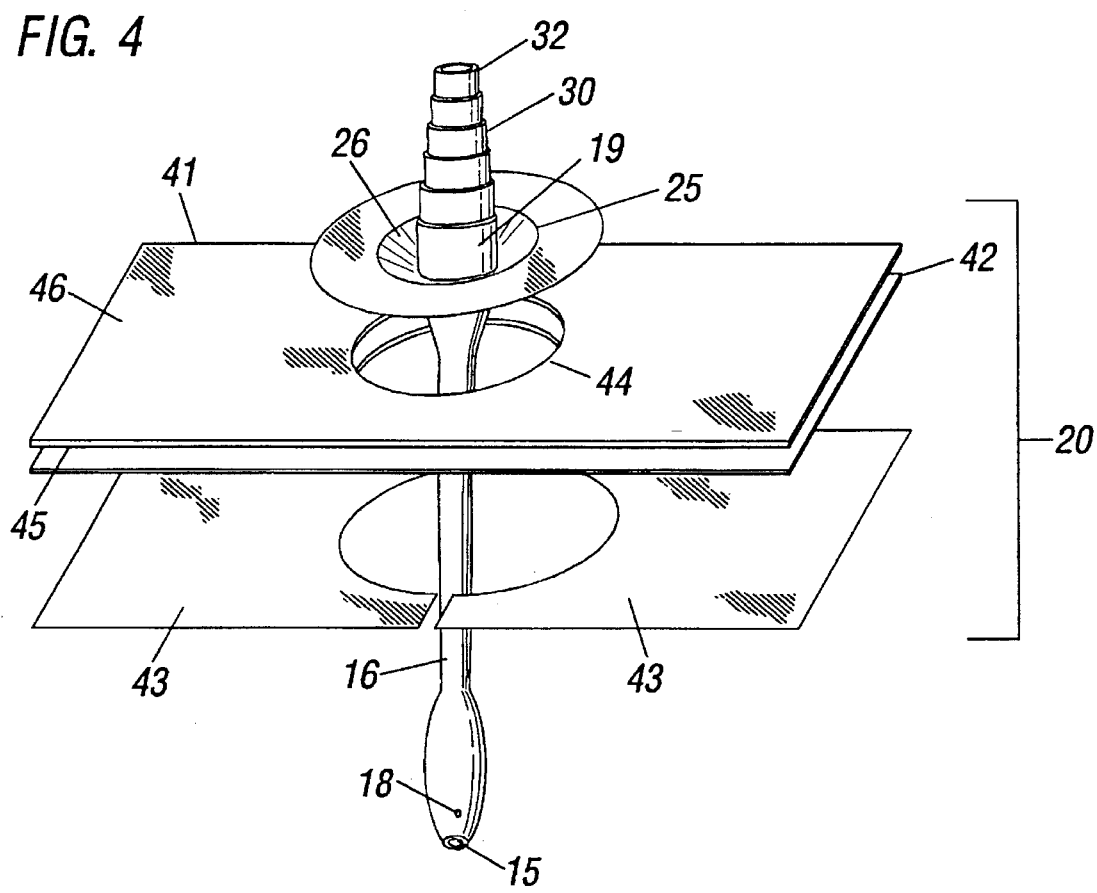
FIG. 4 is a partially exploded view of the positioning collar showing how the self-adhesive sheet attaches to the flat collar extension and how the protective tabs cover the adhesive coating on the underside of the sheet.
Figure 5:
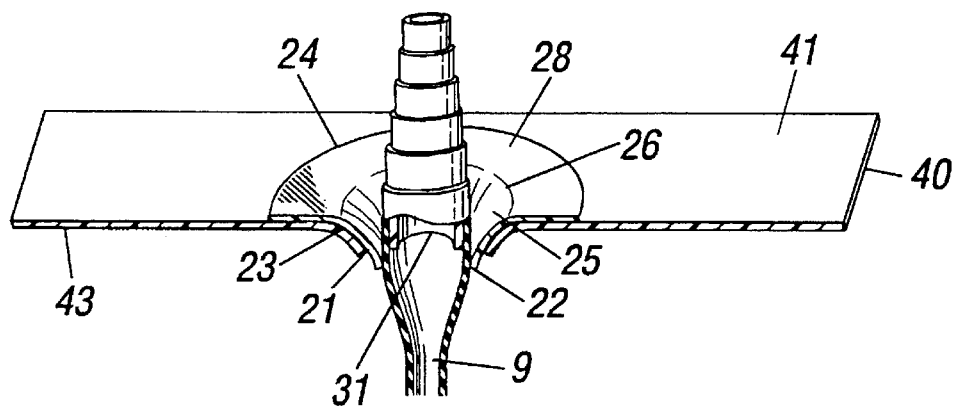
FIG. 5 is an enlarged cross-sectional side view of the distal tube end, with adaptor attached, showing its placement relative to the positioning collar in one embodiment of the invention.
Figure 6:
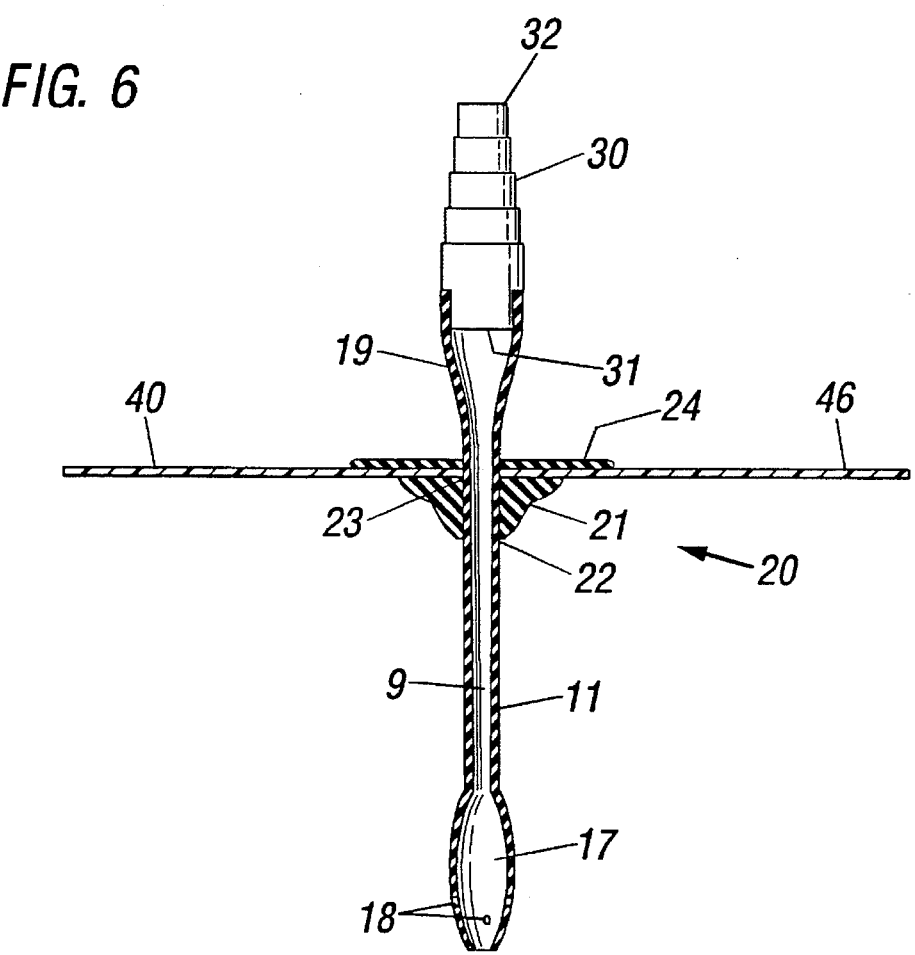
FIG. 6 is a cross-sectional side view of an alternate embodiment of the nozzle showing the adjustable positioning collar set in an intermediate position along the tube away from the site where the adapter joins the tube.

Referring to FIGS. 1, 4 and 5, the disclosed invention further comprises a positioning collar 20 annularly attached to tube 10 at least by friction fit in orifice 22 of frustoconical nipple 21 of the positioning collar 20. The exact manner of attachment is described in more detail below. In one embodiment the positioning collar 20 is fixedly attached at a predetermined distance from end 7 along expanded portion 19 of tube 10. Positioning collar 20 is permanently joined to expanded portion 19. Alternatively, tube 19 and nipple 21 may be molded as one unit thereby eliminating the joint.

In an alternative embodiment, expanded portion 19 provides a backstop for controlling the most distal position along tube 10 the positioning collar 20 can reach. In this embodiment positioning collar 24 is slidably attached to tube 10 at any point along shaft 11 thereby permitting the technologist to adjust the tube length which can be inserted into the rectum. The slidable disposition of collar 24 is accomplished by the annular attachment about shaft 11 of frustoconical nipple 21 at its orifice 22; said attachment having sufficient resistance to incidental sliding to maintain a manually preset position while being resilient enough to permit the desired movement. As shown in FIGS. 1–5, tube 10 extends through nipple orifice 22 of frustoconical nipple 21 of positioning collar 20. End 13, therefore, protrudes into and through frustoconical recess 24, the same being the interior or reverse side of frustoconical nipple 21, best shown in FIGS. 2 and 4.

In one embodiment of the disclosed invention, frustoconical nipple 21 is about 0.8 inches (8 mm) in length, and has an increasing external diameter of about 0.55 to 0.9 inches (5.5 to 9 mm) from orifice 22 to base 23 and frustoconical recess 25 has a correspondingly increasing internal diameter of about 3.5 mm to 2.5 cm from orifice 22 to base 26. Orifice 22 of frustoconical nipple 21 has a diameter of about 11 mm and nipple 21 has a base 23 diameter of about 12 mm. Although the embodiments of the invention disclosed herein describe the positioning collar 24 as having a nipple 21 and recess 25 which are frustoconical in shape, they may be shaped otherwise so long as the nipple 21, recess 25, orifice 22 and bases 22, 23 together constitute sufficient support for the flat collar extension 24, provide adequate frictional contact surface around shaft 11 and provide an attachable surface in fixed collar embodiments of the present invention.

Figure 3:
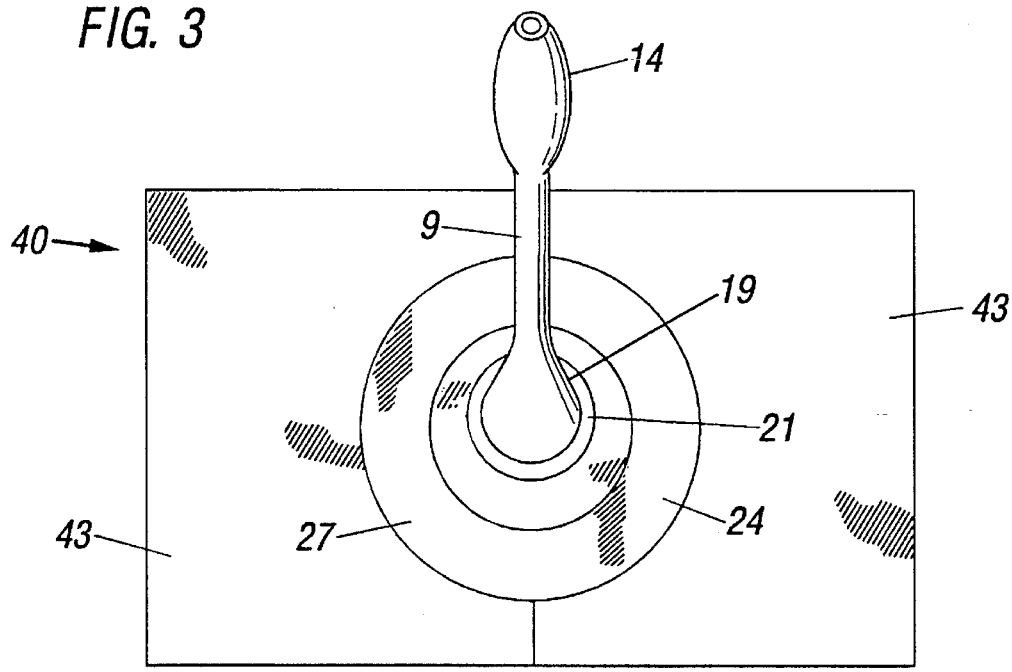
FIG. 3 is a bottom view of one embodiment of the nozzle showing the proximal terminus opening, the tube end joined to the frustoconical nipple, the adhesive side of the self-adhesive sheet with protective tabs in place (wherein one tab is partially peeled back exposing the adhesive).

Referring now to FIGS. 3 and 4, joined to and integral with frustoconical nipple base 3 is flat collar extension 24 which comprises a flat base extension 24 extending axially outward from the respective bases 23, 26 of frustoconical nipple 21 and frustoconical recess 25. The flat collar extension 24 of one embodiment of the present invention has an inner diameter of about 11 mm at the nipple base 23, an outer diameter of about 18 mm, and is about 1 mm thick.

The tube 10, nipple 21, recess 25 and flat collar extension 24 are made of any suitable flexible plastic material, such as polyvinylchloride, and may all be made of the same or different plastic, so long as the combined units provide a nozzle 1 of functionally sufficient rigidity and flexibility. The elongate sheet 41 is made of any suitable flexible material, such as polyethylene plastic. Adhesive layer 42 is any suitable adhesive for contacting the skin. The protective tabs 43 are made of any suitable peelable material. Adapter 30 is made from any suitable rigid plastic and may be a commercially available tubing connector or adapter available from well known sources.

The flat collar extension 24 of the embodiments illustrated herein is round, but it may also be rectangular, square, or any suitable shape or size that will adequately support self-adhesive sheet 40 for its intended use.

Nozzle 1 of the present invention is constructed by pushing terminus 14 of tube 10 through recess 25 and out of nipple 21 through orifice 22 until positioning collar 20 is situated at the desired position along the longitudinal axis of tube 10. Alternatively, positioning collar 20 of the invention may be put into place prior to attachment of terminus 14 to shaft 11 by inserting end 12 of shaft 11 through recess 25 and out nipple 21 through orifice 22 until positioning collar 20 is situated at the desired position along the longitudinal axis of tube 10. In one embodiment of the invention disclosed herein a conventional nipple colostomy tip, such as catalog no. 9517 of Therapex, div. of E-Z-EM, Inc., 7 Portland Ave., Westbury, N.Y. 11590, was modified for use as positioning collar 20 by removing a portion of the tip to form a frustoconical nipple 21.

Flat collar extension 24 has a first surface 27 which faces the patient's body when the nozzle is in use and has a second surface 28 which faces away from the body. Self-adhesive sheet 40 comprises an elongated sheet 41 or strip of flexible plastic firmly attached by thermal bonding or gluing to first surface 27 of extension 24. Elongate sheet 41 is of sufficient length and width to securely attach to and hold the patient's buttocks against tube 10. In one embodiment intended for use on an infant, the elongate sheet is about 25×40 mm and has an annular opening 44 of about 5 mm diameter through which frustoconical nipple 21 protrudes about midway.

As best shown in the exploded view of FIG. 4, self-adhesive sheet 40 further comprises a suitable adhesive layer 42 which coats the underside or first surface 45 of elongate sheet 41 for sticking to the patient's buttocks. In one embodiment of the invention, the area coated by adhesive excludes that portion of the elongate sheet 41 which overlies frustoconical nipple 21 and flat collar extension 24. At least two plastic protective tabs 43 peelably overlie adhesive layer 42 for covering the adhesive until ready for adhering to the skin. Although a rectangular shape has been shown by the inventors to be a suitable shape, the size and shape of elongate sheet 41 are not critical so long as it adequately attaches to the collar extension 24 and sufficiently secures to the patient's buttocks.

When employed in an enema procedure such as, for example, a pediatric radiological barium enema, a tubing leading from an enema bag (not shown) is connected to adapter 30 of the invention disclosed herein. Tube 10 is lubricated with a suitable lubricant such as petroleum jelly, K-Y Jelly™, or Surgilube™, and terminus 14 and shaft 11 are inserted into the child's rectum approximately two inches. While tube 10 is held by the technologist in the desired position relative to the patient's body the positioning collar 20 is oriented with the elongated dimension of the self-adhesive sheet 40 extending transversely across the patient's buttocks. The technologist peels off the protective tabs 43 exposing the adhesive layer 42 of self-adhesive sheet 40. Alternatively, the positioning collar 20 of one embodiment of the invention may be adjusted to a position along tube 10 that is closer to or further from the end 15 of tube 10 as may be necessary, depending on such factors as the age of the child or the size of the buttocks, prior to stripping away the tabs 43. The buttocks may be compressed together to better secure tube 10 in place while the non-adhesive second surface 46 of elongate sheet 41 is pressed down against the buttocks to adhere adhesive layer 42, thereby anchoring positioning collar 20 and thereby securing nozzle 1. The barium fluid is then allowed to flow through tube 10 and out into the patient's rectum through end 15 and auxiliary outlets 18 while being monitored by fluoroscope. When enough barium is in the colon, the radiologist has the patient turn in several different positions for visualizing specific parts of the colon fluoroscopically. The technologist prepares the required number of x-ray films, turning the patient into different positions as needed. Only after the films are developed and checked is the barium solution drained out of the patient through tube 10 and into the bag, and the tube 10 removed. Post evacuation films are then taken to complete the procedure.

From the above description of a barium enema procedure employing the disclosed nozzle, it can readily be seen how the secure placement of the enema nozzle for the required time and throughout numerous repositionings of the patient is essential to the success of the procedure. Other advantages which can be appreciated by those of skill in the art is the elimination of the need for attachment of other materials to secure the nozzle such as, for example, wrapping surgical tape around the tube and strapping it to the patient. The self-adhesive layer of the present invention is easily readied by the technologist and secured to the buttocks. Both expulsion of the tube and migration of the tube too far internally during the procedure is avoided because of the stable attachment of the device to the buttocks. In addition, the disclosed device provides more comfort for the patient because it is adhesively anchored to the buttocks rather than contacting the body elsewhere. The nozzle of the invention can be more quickly positioned by the technologist than prior art devices, and is less cumbersome for the patient to wear than prior art devices. The problem of leakage is minimized by the nozzle of the present invention because the patient's buttocks are firmly held together against the tube by the self adhesive strip. In particular, the disclosed nozzle is advantageous for use in infants, young children, the infirm and the elderly by lessening the risk of injury to the patient's rectal wall from unanticipated shifting of the tube and by avoiding use of an inflation balloon.

While the preferred embodiments of the invention have been shown and described, modifications thereof can be made by one skilled in the art without departing from the spirit and teachings of the invention. The embodiments described herein are exemplary only, and are not limiting. Many variations and modifications of the invention and apparatus disclosed herein are possible and are within the scope of the invention. Accordingly, the scope of protection is not limited by the description set out above, but is only limited by the claims which follow, that scope including all equivalents of the subject matter of the claims.

What is claimed is:

1. A disposable enema nozzle comprising:
   a flexible plastic tube having a first bulbous end and a second end separated by a shaft, said first end and shaft being adapted to fit into a patient's rectum;
   a fluid path through said tube;
   a conduit connector attached to and in fluid communication with said second end;
   a flexible positioning collar annularly attached to said tube and extending radially outward from said tube, said positioning collar comprising self-adhesive means adapted for securing said positioning collar to a patient's buttocks, said nozzle being adapted to compress the buttocks against said tube when said tube is positioned in the rectum.

2. The nozzle of claim 1 wherein said positioning collar comprises:
   a flexible plastic nipple having a base and an annular orifice, said orifice being disposed about said tube;
   a recess defined by said nipple, said recess having a base;
   a flat collar extension, comprising:
      a first and a second surface formed integrally with and extending radially outward from the respective bases of the nipple and recess; and
      a self-adhesive sheet fixedly attached to the first surface of said flat collar extension, said self-adhesive sheet, comprising:
         an elongate flexible plastic sheet having a first and a second surface and an opening, said second surface being fixedly attached to the first surface of the flat collar extension permitting said tube to extend through said opening;
         an adhesive layer overlying the first layer of said flexible plastic sheet; and
         at least two protective tabs peelably attached to said adhesive layer.

3. The nozzle of claim 2 wherein said nipple and recess are frustoconical said frustoconical nipple extends at least partially through the opening in said elongate flexible plastic sheet, and said nipple is fixedly attached to said tube.

4. The disposable enema nozzle of claim 1 wherein said tube comprises:
   a shaft having a fluid path therethrough and having a first and a second end;
   a flexible plastic terminus having a fluid path therethrough in communication with that of said shaft, and having a first and a second end;
      said terminus first end being the entry point for placement in a patient's rectum, and said second terminus end being joined end-to-end with said shaft first end; and
   an expanded portion having a first and a second end, said expanded portion first end being integral with and connected to the shaft second end and said expanded portion second end being attached to and in fluid communication with said conduit connector;
   wherein said positioning collar is fixedly attached to a point about midway along said tube expanded portion and further comprises:
      a flexible plastic frustoconical nipple slidably disposed about said tube, a frustoconical recess defined by said frustoconical nipple, a flat collar extension, comprising:
         a first and a second surface, formed integrally with and extending radially outward from the respective bases of the frustoconical nipple and frustoconical recess; and
         a self-adhesive sheet fixedly attached to the first surface of said flat collar extension comprising:
            an elongate flexible plastic sheet having an annular opening through which the frustoconical nipple protrudes about midway, said plastic sheet being firmly affixed to the corresponding area of the flat collar extension first surface,
            a suitable adhesive coating on the flexible sheet first layer, exclusive of the sheet portion which is firmly affixed to the flat collar extension, and
            at least two peelable protective tabs overlying the adhesive coating.

5. The enema nozzle of claim 1 wherein said positioning collar is slidably attached to said tube for adjusting the tube length which can be inserted into the rectum, said slidable attachment having sufficient resistance to incidental sliding to maintain a manually preset collar position.

6. The nozzle of claim 5 wherein said positioning collar comprises:
   a flexible plastic nipple having a base and an annular orifice, said orifice being slidably disposed about said tube;
   a recess defined by said nipple and having a base;
   a flat collar extension, comprising:
      a first and a second surface formed integrally with and extending radially outward
      from the respective bases of the nipple and recess; and
      a self-adhesive sheet fixedly attached to the first surface of said flat collar extension and adhesively attachable to a patient's buttocks.

7. The nozzle of claim 6 wherein the nipple and recess are frustoconical.

8. The enema nozzle of claim 6 wherein said self-adhesive sheet comprises:
   an elongate flexible plastic sheet having a first and a second surface, said second surface being fixedly attached to the first surface of the flat collar extension,
   an adhesive layer overlying the first layer of said flexible plastic sheet; and
   at least two protective tabs peelably attached to said adhesive layer.

9. A disposable enema nozzle according to claim 7 wherein said tube comprises:
   a shaft having a fluid path therethrough and having a first and a second end;
   a flexible plastic terminus having a fluid path therethrough in communication with that of said shaft, and having a first and a second end;
   said terminus first end being the entry point for placement in a patient's rectum, and said second terminus end being joined end-to-end with said shaft first end; and
   an expanded portion having a first and a second end, said expanded portion first end being integral with and connected to the shaft second end and said expanded portion second end being attached to and in fluid communication with said conduit connector; and
   wherein said positioning collar is slidably attached to a preselected point along said tube, said positioning collar comprising:

an elongate flexible plastic sheet having an annular opening through which the frustoconical nipple protrudes about midway, said plastic sheet being firmly affixed to the corresponding area of the flat collar extension first surface, a suitable adhesive coating on the flexible sheet first layer, exclusive of the sheet portion which is firmly affixed to the flat collar extension, and at least two peelable protective tabs overlying the adhesive coating.

10. The nozzle of claim 9 wherein said terminus is ovoid in shape and wherein said nozzle is adapted for rectal administration of an enema to a pediatric patient.

11. The improved nozzle of claim 12 wherein said tube comprises a first bulbous end distal to said positioning collar.

12. An improved disposable enema nozzle including a flexible plastic tube and means for securing the nozzle to the body, wherein the improvement comprises:

a positioning collar annularly attached to said tube, said positioning collar comprising:

a flexible plastic frustoconical nipple having a base and an orifice being disposed about said tube at a preset point on the tube, a frustoconical recess defined by said frustoconical nipple and having a base, a flat collar extension, comprising:

first and second surfaces, formed integrally with and extending radially outward from the respective bases of the frustoconical nipple and frustoconical recess, and a self-adhesive sheet comprising:

an elongate flexible plastic sheet having first and second surfaces and an opening, said second surface being fixedly attached to the first surface of the flat collar extension permitting said frustoconical nipple to protrude at least partially through said opening, an adhesive layer overlying the first layer of said flexible plastic sheet; and at least two protective tabs peelably attached to said adhesive layer, said tube being adapted for placement in a patient's rectum and said positioning collar and tube being adapted to compress the buttocks against said tube when said positioning collar and tube are positioned for administration of an enema.

13. The improved nozzle of claim 12 wherein said nipple orifice is fixedly attached at a preset position along the longitudinal axis of said tube.

14. The improved nozzle of claim 12 wherein said nipple orifice is slidingly attached at a preset position along the longitudinal axis of said tube, said slidable attachment having sufficient resistance to incidental sliding to maintain said position.

15. A positioning collar for securing an enema tube in a patient's rectum during an enema procedure comprising:

a flexible plastic nipple having a base and an annular orifice, said orifice being capable of being attached to said tube at a preset point along the longitudinal axis of said tube;

a recess defined by said nipple and having a base;

a flat collar extension, comprising:

a first and a second surface, formed integrally with and extending radially outward from the respective bases of the nipple and recess, and a self-adhesive sheet fixedly attached to the first surface of said flat collar extension, said self-adhesive sheet comprising:

an elongate flexible plastic sheet having a first and a second surface, said second surface being fixedly attached to the first surface of the flat collar extension;

an adhesive layer overlying the first layer of said flexible plastic sheet adapted for adhering said self-adhesive sheet to the patient's buttocks, whereby the buttocks are compressed against said tube when said positioning collar and tube are positioned for administration of an enema; and at least two protective tabs peelably attached to said adhesive layer.

16. The positioning collar of claim 15 wherein said nipple and recess are frustoconical.

17. The positioning collar of claim 15 wherein said annular orifice is capable of being slidably attached to said tube at a preset point along said tube's longitudinal axis such that said slidable attachment is sufficiently resistant to incidental sliding to permit a manually preset collar position to be maintained during use of said tube.

* * * * *